United States Patent
Jia

(10) Patent No.: US 9,623,058 B2
(45) Date of Patent: Apr. 18, 2017

(54) BACTERIOPHAGES

(71) Applicant: AMPLIPHI BIOSCIENCES CORPORATION, Richmond, VA (US)

(72) Inventor: Ying Jia, Chorley (GB)

(73) Assignee: Ampliphi Biosciences Corporation, Richmond, VA (US)

( * ) Notice: Subject to any disclaimer, the term of this patent is extended or adjusted under 35 U.S.C. 154(b) by 0 days.

(21) Appl. No.: 14/356,869

(22) PCT Filed: Nov. 7, 2012

(86) PCT No.: PCT/GB2012/052770
§ 371 (c)(1),
(2) Date: May 7, 2014

(87) PCT Pub. No.: WO2013/068743
PCT Pub. Date: May 16, 2013

(65) Prior Publication Data
US 2014/0322174 A1    Oct. 30, 2014

(30) Foreign Application Priority Data

Nov. 7, 2011 (GB) .................................. 1119167.3

(51) Int. Cl.
*A61K 35/76* (2015.01)
*C12N 7/00* (2006.01)
*A61K 9/00* (2006.01)

(52) U.S. Cl.
CPC ............ *A61K 35/76* (2013.01); *A61K 9/0014* (2013.01); *A61K 9/0043* (2013.01); *C12N 7/00* (2013.01); *C12N 2795/10121* (2013.01); *C12N 2795/10131* (2013.01)

(58) Field of Classification Search
None
See application file for complete search history.

(56) References Cited

FOREIGN PATENT DOCUMENTS

| JP | 2011-501740 | 1/2011 |
|----|----|----|
| WO | WO 2009/044163 | 4/2009 |

OTHER PUBLICATIONS

Kelly et al. (Bioengineered Bugs 2:1, 31-37, 2011).*
GenBank: HQ163896.1, Staphylococcus phage Sb-1, complete genome, Jul. 11, 2011.
Kvachadze, L. et al., "Evaluation of lytic activity of staphylococcal bacteriophage Sb-1 against freshly isolated clinical pathogens," Microbial Biotechnology, vol. 4, No. 5, pp. 643-650 (2011).
Kelly, D. et al., "Development of a broad-host-range phage cocktail for biocontrol," Bioengineered Bugs, vol. 2, No. 1, pp. 31-37 (2011).
O'Flaherty, S. et al., "Genome of Staphylococcal Phage K: a New Lineage of Myoviridae Infecting Gram-Positive Bacteria with a Low G+C Content," J. Bacteriol., vol. 186 No. 9, pp. 2862-2871 (May 2004).
O'Flaherty, S. et al., "Potential of the polyvalent anti-Staphylococcus bacteriophage K for control of antibiotic-resistant staphylococci from hospitals," Applied and Environmental Microbiology, vol. 71, No. 4, pp. 1836-1842 (Apr. 2005).
Weidenmaier, C. et al., "Differential roles of sortase-anchored surface proteins and wall teichoic acid in *Staphylococcus aureus* nasal colonization," International Journal of Medical Microbiology, vol. 298, No. 5-6, pp. 505-513 (Jul. 2008).
Xia, G. et al., "Wall Teichoic Acid-Dependent Adsorption of Staphylococcal Siphovirus and Myovirus," Journal of Bacteriology, vol. 193, No. 15, pp. 4006-4009 (Aug. 2011; online Jun. 3, 2011).
Shaw, D. R. D. et al., "Ribitol Teichoic Acid Synthesis in Bacteriophage-resistant Mutants of *Staphylococcus aureus* H*," The Journal of Biological Chemistry, vol. 245, No. 19, pp. 5101-5106 (Oct. 1970).
International Search Report and Written Opinion for International Application No. PCT/GB2012/052770, mailed Apr. 26, 2013, 19 pages.

* cited by examiner

*Primary Examiner* — Brian J Gangle

(57) ABSTRACT

The present invention provides a bacteriophage with effective antibacterial activity against *Staphylococcus* strains and in particular MRSA. There is also provided a pharmaceutical composition comprising said bacteriophage and a method of treating a bacterial infection using a composition comprising said bacteriophage.

18 Claims, 2 Drawing Sheets

SEQUENCE LISTING

<160> NUMBER OF SEQ ID NOS: 20

<210> SEQ ID NO 1
<211> LENGTH: 24
<212> TYPE: DNA
<213> ORGANISM: Artificial
<220> FEATURE:
<223> OTHER INFORMATION: PCR primer

<400> SEQUENCE: 1
tggcatagca agagcttcat caac                                          24

<210> SEQ ID NO 2
<211> LENGTH: 24
<212> TYPE: DNA
<213> ORGANISM: Artificial
<220> FEATURE:
<223> OTHER INFORMATION: PCR Primer

```
<400> SEQUENCE: 2
agcagaaagt gtcaagggag ttag                                        24

<210> SEQ ID NO 3
<211> LENGTH: 20
<212> TYPE: DNA
<213> ORGANISM: Artificial
<220> FEATURE:
<223> OTHER INFORMATION: PCR Primer

<400> SEQUENCE: 3
ctagatgcgg aacccggtag                                             20

<210> SEQ ID NO 4
<211> LENGTH: 24
<212> TYPE: DNA
<213> ORGANISM: Artificial
<220> FEATURE:
<223> OTHER INFORMATION: PCR Primer

<400> SEQUENCE: 4
tgcagggtca ataccatata aagc                                        24

<210> SEQ ID NO 5
<211> LENGTH: 22
<212> TYPE: DNA
<213> ORGANISM: Artificial
<220> FEATURE:
<223> OTHER INFORMATION: PCR Primer

<400> SEQUENCE: 5
ttggacttca ccaaaaacat cc                                          22

<210> SEQ ID NO 6
<211> LENGTH: 21
<212> TYPE: DNA
<213> ORGANISM: Artificial
<220> FEATURE:
<223> OTHER INFORMATION: PCR Primer

<400> SEQUENCE: 6
acgcagggct gtactgaaat c                                           21

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
gttccgttgc tcacggtaaa c                                           21

<210> SEQ ID NO 8
<211> LENGTH: 24
<212> TYPE: DNA
<213> ORGANISM: artificial
<220> FEATURE:
<223> OTHER INFORMATION: PCR primer

<400> SEQUENCE: 8
tccccattta agaatgattg tagc                                        24

<210> SEQ ID NO 9
```

-continued

<210> SEQ ID NO 9
<211> LENGTH: 21
<212> TYPE: DNA
<213> ORGANISM: Artificial
<220> FEATURE:
<223> OTHER INFORMATION: PCR primer

<400> SEQUENCE: 9
tctcagcaac tgaagcattc c                                              21

<210> SEQ ID NO 10
<211> LENGTH: 22
<212> TYPE: DNA
<213> ORGANISM: Artificial
<220> FEATURE:
<223> OTHER INFORMATION: PCR primer

<400> SEQUENCE: 10
acctgtgaat catcaacact gc                                             22

<210> SEQ ID NO 11
<211> LENGTH: 21
<212> TYPE: DNA
<213> ORGANISM: Artificial
<220> FEATURE:
<223> OTHER INFORMATION: PCR Primer

<400> SEQUENCE: 11
accaaaggag catggagaaa c                                              21

<210> SEQ ID NO 12
<211> LENGTH: 21
<212> TYPE: DNA
<213> ORGANISM: Artificial
<220> FEATURE:
<223> OTHER INFORMATION: PCR Primer

<400> SEQUENCE: 12
gggaatccac cttcttcaat g                                              21

<210> SEQ ID NO 13
<211> LENGTH: 25
<212> TYPE: DNA
<213> ORGANISM: Artificial
<220> FEATURE:
<223> OTHER INFORMATION: PCR Primer

<400> SEQUENCE: 13
ttctcaaatg attcaggaga gtcag                                          25

<210> SEQ ID NO 14
<211> LENGTH: 22
<212> TYPE: DNA
<213> ORGANISM: Artificial
<220> FEATURE:
<223> OTHER INFORMATION: PCR Primer

<400> SEQUENCE: 14
ccattacttt cccctccttt tc                                             22

<210> SEQ ID NO 15
<211> LENGTH: 23
<212> TYPE: DNA
<213> ORGANISM: Artificial
<220> FEATURE:
<223> OTHER INFORMATION: PCR Primer

<400> SEQUENCE: 15

-continued

```
ggtaagtcaa ggacaacctc cac                                              23

<210> SEQ ID NO 16
<211> LENGTH: 20
<212> TYPE: DNA
<213> ORGANISM: Artificial
<220> FEATURE:
<223> OTHER INFORMATION: PCR Primer

<400> SEQUENCE: 16
aggtgttcct cccggtattg                                                  20

<210> SEQ ID NO 17
<211> LENGTH: 25
<212> TYPE: DNA
<213> ORGANISM: Artificial
<220> FEATURE:
<223> OTHER INFORMATION: PCR Primer

<400> SEQUENCE: 17
acagcatacg ttctaaagga acaag                                            25

<210> SEQ ID NO 18
<211> LENGTH: 23
<212> TYPE: DNA
<213> ORGANISM: Artificial
<220> FEATURE:
<223> OTHER INFORMATION: PCR Primer

<400> SEQUENCE: 18
ccctacgatt atttgggcta aag                                              23

<210> SEQ ID NO 19
<211> LENGTH: 25
<212> TYPE: DNA
<213> ORGANISM: Artificial
<220> FEATURE:
<223> OTHER INFORMATION: PCR Primer

<400> SEQUENCE: 19
agctgataaa gaccctagaa caacg                                            25

<210> SEQ ID NO 20
<211> LENGTH: 24
<212> TYPE: DNA
<213> ORGANISM: Artificial
<220> FEATURE:
<223> OTHER INFORMATION: PCR primer

<400> SEQUENCE: 20
tgtaaccacc gctaatacaa tctg                                             24
```

BACTERIOPHAGES

FIELD OF THE INVENTION

The invention relates to a *Staphylococcus* bacteriophage K mutant, which comprises one or more mutations within one or more selected regions of the corresponding nucleotide sequence of wild-type *Staphylococcus* bacteriophage K (Accession number: AY176327.1), to the use of said bacteriophage in the treatment of a bacterial infection, to a pharmaceutical composition comprising said bacteriophage and to a method of treating a bacterial infection using a composition comprising said bacteriophage.

BACKGROUND OF THE INVENTION

In recent years the widespread use of antibacterial agents, in the form of chemically-based antibiotics, such as penicillin or tetracycline, has led to a huge increase in antibiotic-resistant bacterial strains. Mutations conferring antibiotic resistance, or genes encoding antibiotic resistance enzymes, such as penicillinases, are becoming increasingly common in pathogenic bacteria world-wide. Methicillin-resistant *Staphylococcus aureus* (MRSA) bacteria, for example, are an increasingly common form of infection, often acquired during surgery for other causes at hospitals. MRSA infections are extremely difficult to treat using conventional antibiotics.

One alternative approach to treating bacterial infections with antibiotics is to infect the bacteria with a virus, known as a bacteriophage. Such "bacteriophage therapy" was first developed early in the twentieth century, but was rarely used in the West after the advent of antibiotics in the 1940s.

Bacteriophages are specific to certain bacterial cell types. They cannot infect the cells of more complex organisms because of the differences in key intracellular machinery and cell-surface components. Most bacteriophages have structures, such as tail fibers, which enable them to bind to specific molecules on the surface of their target bacteria. Viral DNA, usually encased within the bacteriophage head, or RNA in some bacteriophages, is then injected, usually through the tail, into the host cell. In the case of obligate lytic phages, the injected viral DNA/RNA goes on to direct the production of bacteriophage progeny using the intracellular mechanisms of the host cell. The host cell is killed by lysis at the end of the cell cycle.

*Staphylococcus* bacteriophage K is a member of the diverse Myoviridae bacteriophage family. A paper by O'Flaherty S. et al. (J. Bacteriol. (2004), 186(9) 2862-2871) describes the sequence of the DNA genome of Staphylococcal phage K which carries 118 putative open reading frames (ORFs). Phage K has been previously characterized as an anti-MRSA phage. O'Flaherty S. et al. (Appl. Environ. Microbiol. (2005), 71(4) 1836-1842) studied phage K on different drug-resistant strains of *S. aureus*.

WO 2009/044163 describes an anti-bacterial composition comprising phage K and/or phage P68 in a sufficiently high concentration to induce lysis-from-without in bacteria.

Methicillin-resistant *Staphylococcus aureus* (MRSA) can cause systemic infections or abscesses and ulcers, especially in sick, elderly or immune-compromised patients. It is increasingly a major cause of, or contribution to, death in hospitals. MRSA may reside in the nasal cavity of doctors or visitors without any apparent disease symptoms. However, the bacteria may be spread from person to person, including to patients. Accordingly, killing the bacteria assists in the prevention of the disease.

Hospitals currently utilise alcoholic hand-washes to help prevent MRSA being transmitted. However, such alcoholic washes are often not suitable for use on the sensitive lining of the nasal cavity or broken areas of skin. Therefore, there is a need to produce a composition suitable for killing bacteria, such as *Staphylococcus aureus* and in particular MRSA.

An object of the invention is to provide an alternative bacteriophage which provides effective antibacterial activity against *Staphylococcus* strains and in particular MRSA.

SUMMARY OF THE INVENTION

According to a first aspect of the invention, there is provided a *Staphylococcus* bacteriophage K mutant, which comprises one or more mutations within one or more of the following regions, corresponding to the nucleotide sequence of wild-type *Staphylococcus* bacteriophage K (Accession number: AY176327.1), selected from:
  a) the region between ORF 18 and ORF 19; and/or
  b) the region between ORF 41 and ORF 42; and/or
  c) ORF 68; and/or
  d) an overlapping region within ORF 86/88/90; and/or
  e) ORF 92; and/or
  f) ORF 93; and/or
  g) ORF 96; and/or
  h) ORF 100.

According to a further aspect of the invention there is provided a bacteriophage, as defined herein, for use in the treatment of a bacterial infection.

According to a further aspect of the invention there is provided a pharmaceutical composition comprising a bacteriophage as defined herein, and a pharmaceutically acceptable carrier thereof.

According to a further aspect of the invention there is provided a method of treating a bacterial infection, comprising applying a composition as defined herein, to an infected surface.

DETAILED DESCRIPTION OF THE INVENTION

Figure 1:
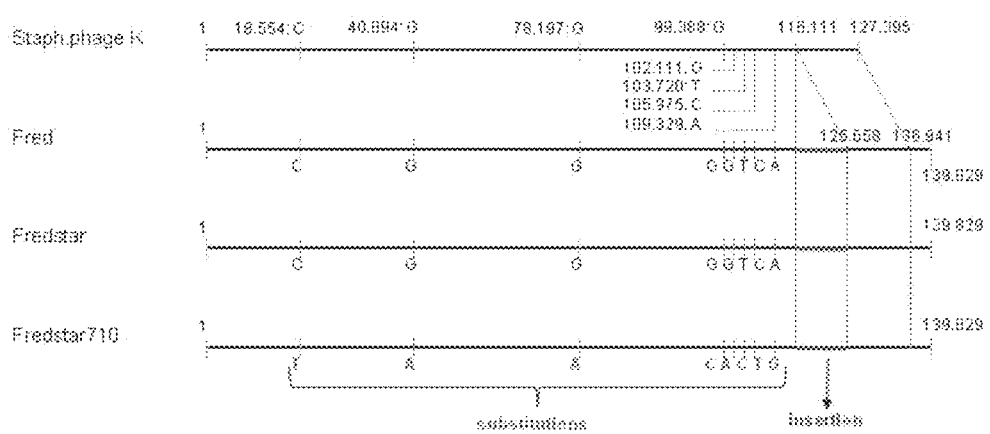
FIG. 1: Diagram showing a comparison of the DNA sequences of the four phages in Example 2 (*Staphylococcus* bacteriophage K, 'Fred', 'Fred*' and 'Fred*710').

According to a first aspect of the invention, there is provided a *Staphylococcus* bacteriophage K mutant, which comprises one or more mutations within one or more of the following regions, corresponding to the nucleotide sequence of wild-type *Staphylococcus* bacteriophage K (Accession number: AY176327.1), selected from:
  a) the region between ORF 18 and ORF 19; and/or
  b) the region between ORF 41 and ORF 42; and/or
  c) ORF 68; and/or
  d) an overlapping region within ORF 86/88/90; and/or
  e) ORF 92; and/or
  f) ORF 93; and/or
  g) ORF 96; and/or
  h) ORF 100.

References herein to "*Staphylococcus* bacteriophage K" refer to the well-characterized type of bacteriophage as described in O'Flaherty S. et al. (J. Bacteriol. (2004), 186(9) 2862-2871). Such references include equivalent terms such as "Staphylococcal phage K" or "phage K". Phage K is a bacteriophage that has been found to have activity against a wide range of staphylococcal strains.

It has been surprisingly found that development of phage K derivatives has revealed particular mutations to the wild type phage K genome which can give rise to a broader spectrum of antimicrobial action. The phage mutants of the invention therefore provide the advantage of using a single type of bacteriophage to treat a wider range of bacterial strains within a given bacterial species.

References herein to "mutant" refer to a bacteriophage with a different genotype to the wild-type bacteriophage. Such a mutant may also result in a phenotypic difference.

References herein to "mutation" refer to a change in a genomic sequence. The DNA sequences can be changed in a variety of ways, such as through point mutations, insertions, deletions and duplications. Point mutations occur when one base is substituted for another. For example, a transition point mutation is when a purine base is substituted for a different purine base (i.e. adenine (A) is substituted for guanine (G) or vice versa) or a pyrimidine base is substituted for a different pyrimidine base (i.e. thymine (T) is substituted for cytosine (C) or vice versa). In another example, a transversion point mutation is when a purine is substituted for a pyrimidine or vice versa, such as A is substituted for T or C, G is substituted for T or C, T is substituted for A or G, or C is substituted for A or G.

Mutations can be caused spontaneously or be induced, for example by chemicals, radiation or viral infection. One way of inducing a mutation is by using a mutagenic chemical agent, such as hydroxylamine.

References herein to "ORF" or "Open Reading Frame" refer to a portion of the nucleotide sequence between a start codon and a stop codon in the same reading frame. Stop codons are a triplet of nucleotides that act as a signal to stop translation. This includes the DNA nucleotide sequences "TGA", "TGG" and "TAG". Phage K has been identified to have 118 putative ORFs.

In one embodiment, the mutation occurs within ORF 96 of the corresponding nucleotide sequence of wild-type *Staphylococcus* bacteriophage K (Accession number: AY176327.1). ORF 96 has been identified in phage K to encode a putative major tail protein.

In a further embodiment, the mutation is a C105975T point mutation of the corresponding nucleotide sequence of wild-type *Staphylococcus* bacteriophage K (Accession number: AY176327.1).

It will be acknowledged point mutations from herein will be referred to with the following annotation: (base in wild-type phage K genome)(position)(base in phage K mutant). For example, C105975T describes a cytosine base in the wild-type phage K genome, at position 105975, has been substituted with a thymine base in the phage K mutant. This mutation results in an alanine being substituted for a valine residue.

In a further embodiment, the bacteriophage additionally comprises one or more of the following point mutations: C18554T, G40894A, G78197A, G99388C, G102111A, T103720C and/or A109329G of the corresponding nucleotide sequence of wild-type *Staphylococcus* bacteriophage K (Accession number: AY176327.1).

The C18554T mutation occurs within the region between ORF 18 and ORF 19 so that a valine is substituted for a methionine residue. The G40894A mutation occurs within the region between ORF 41 and ORF 42 with no predicted amino acid change. The G78197A mutation occurs within ORF 68 resulting in a glycine being substituted for an arginine residue. The G99388C mutation occurs within the region where ORF 86, ORF 88 and ORF 90 overlap, with no predicted amino acid change. The G102111A mutation occurs within ORF 92 resulting in a glycine being substituted for an arginine residue. The T103720C mutation occurs within ORF 93 and results in a silent substitution. Finally, the A109329G occurs within ORF 100 resulting in a lysine being substituted for a glutamate residue.

In one embodiment, the bacteriophage comprises one or more of the following point mutations: C18554T, G40894A, G78197A, G99388C, G102111A, T103720C, C105975T and A109329G of the corresponding nucleotide sequence of wild-type *Staphylococcus* bacteriophage K (Accession number: AY176327.1). Thus, the bacteriophage comprises one, two, three, four, five, six, seven or eight of these mutations in any combination. In a preferred embodiment, the bacteriophage comprises the following point mutations: C18554T, G40894A, G78197A, G99388C, G102111A, T103720C, C105975T and A109329G of the corresponding nucleotide sequence of wild-type *Staphylococcus* bacteriophage K (Accession number: AY176327.1).

In one embodiment, the bacteriophage additionally comprises a further mutation within the nucleotide sequence. Such "further mutations" include any of the various types of mutations, for example, point mutations, deletions, duplications or insertions.

In one embodiment, the further mutation comprises an insertion at position 116111 of the corresponding nucleotide sequence of wild-type *Staphylococcus* phage K (Accession number: AY176327.1).

References herein to "insertion" refer to genetic mutations wherein one or more extra nucleotide bases are added into a nucleotide sequence. Segments of at least one nucleotide can be added into the nucleotide sequence, such as at least 1000, 2000, 3000, 4000, 5000, 6000, 7000, 8000 or at least 9000 bases in length.

In one embodiment the insertion is at least 9000 base pairs in length. In a further embodiment the insertion is 9547 base pairs in length.

According to a further aspect of the invention, there is provided a bacteriophage deposited under accession number: NCIMB 41894 (*S. aureus* phage K*710 described here as Fred*710, deposited under Budapest Treaty on 3 Nov. 2011, together with a suitable *Staphylococcus* host cell under accession number NCIMB 41893).

According to a further aspect of the invention, there is provided a bacteriophage for use in the treatment of a bacterial infection.

Bacteriophages are particularly advantageous to use as a bacterial infection treatment because they are self-replicating, a single bacteriophage may kill a population of millions of host bacteria by virtue of its ability to replicate as an essential part of the killing process. The bacteriophages simply replicate themselves by killing bacteria until they have eliminated them from the individual or the environment. They continue to multiply and develop for as long as the infection is present.

According to a further aspect of the invention, there is provided a pharmaceutical composition comprising the bacteriophage as described herein, and a pharmaceutically acceptable carrier thereof.

The pharmaceutical composition of the present invention may be made according to procedures well known to those skilled in the art and/or are commercially available. Pharmaceutical compositions may be in the form of lotions, creams, ointments, pastes, gels, foams or vapors. Such forms are particularly suitable for topical applications.

In one embodiment, the pharmaceutical composition comprises an additional bacteriophage, such as P68. Pharmaceutical compositions comprising such combinations of bacteriophage K and P68 may be prepared in accordance with the procedures described in WO 2009/044163.

In a further embodiment the pharmaceutical composition is a topical application.

References herein to "topical application" refer to a medicament which can be applied to body surfaces. Many bacterial infections, such as MRSA, are transmitted from person to person via the skin; therefore it is advantageous to have the pharmaceutical composition in the form of a medicament that can be applied to body surfaces such as the skin.

Topical applications may be thickened to form formulations which are particularly advantageous because they adhere to the area of the skin on which the material is placed, thus allowing a localized high concentration of phage to be introduced to a particular area. The formulations may also comprise one or more of the following: water, preservatives, active surfactants, emulsifiers, anti-oxidants or solvents.

In one embodiment the topical application comprises application to the nasal cavity of a mammal.

Certain bacterial infections, such as MRSA, have been found harboring on the mucosal surface within the nasal cavity. Alcoholic washes currently used by hospitals are often not suitable for use on the sensitive lining of the nasal cavity or broken areas of skin. Therefore it is advantageous to have a pharmaceutical composition in the form of a topical application to apply to the nasal cavity.

Paraffin- and lanolin-based creams are well known in the art and are particularly useful for the application of a product to the nasal cavity. Other thickeners, such as polymer thickeners, may also be used.

The use of phage K in the pharmaceutical composition has an additional advantage. Phage K recognizes and binds to Gram positive bacteria via the large amounts of teichoic acid contained in the bacterial cell wall. It has been known since the 1970s that *S. aureus* mutants that are resistant to phage K lack ribitol teichoic acid (Shaw D. R. D. et al., J. Biol. Chem. (1970) 245 (19) 5101-5106). The lack of wall teichoic acids has been found to reduce interactions with epithelial cells, as the teichoic acid is needed for the bacterium to attach to epithelial cells, such as nasal cells (Weidenmaier C. et al., Int. J. Medical Microbiol (2008) 298, 505-513). Hence if teichoic acid is present, phage K should bind to the bacterium. However, if the bacterium mutates to be resistant to phage K by reducing teichoic acid in the cell wall, then this should reduce the ability of the bacterium to bind nasal cells and therefore assist in reducing the virulence of any bacteria remaining after treatment with phage K (Xia, Guoqing et al, Wall Teichoic Acid-Dependent Adsorption of Staphylococcal Siphovirus and Myovirus, Journal of Bacteriology, 193(15), p4006-4009, August 2011).

In one embodiment, the pharmaceutical composition comprises a bacteriophage, as described herein, which is a pathogen of the bacterium *Staphylococcus*.

References herein to "pathogen" indicate the particular bacterium the bacteriophage is capable of binding and infecting. *Staphylococcus* has developed strains with antibiotic resistance so there is a need to be able to treat these infections with antibiotic alternatives, such as by using the bacteriophages of the present invention.

The *Staphylococcus* genus encompasses Gram-positive bacteria that form characteristic "grape-like" clusters.

In a further embodiment, the bacteriophage is a pathogen of *Staphylococcus aureus*.

In a yet further embodiment, the bacteriophage is a pathogen of Methicillin-resistant *Staphylococcus aureus*. MRSA is a strain of *Staphylococcus aureus* that has become resistant to Methicillin and other related antibiotics. Infection by MRSA is a particular concern in hospitals and nursing homes where the patients are particularly vulnerable to infection. It is recommended throughout the healthcare system to restrict the use of antibiotics, to help combat the development of antibiotic resistant strains, and treatment by using the bacteriophages of the present invention provides a suitable alternative.

According to a further aspect of the invention, there is provided a method of treating a bacterial infection, comprising applying the composition as described herein, to an infected surface.

In one embodiment the surface is the skin of a mammal. In a further embodiment the surface is the mucosal membrane or lining, for example within the nasal or oral cavity of a mammal.

Preferred embodiments of the present invention will now be described, merely by way of example, with reference to the following examples.

Example 1

Characterising Novel Bacteriophages a) Roche 454 FLX Library Preparation and Sequencing of the Three Phage DNAs The following three phage DNA samples were used in the characterisation study:

'Fred' was derived from wild type *Staphylococcus* phage K;

'Fred*' was derived from 'Fred' by selection of a spontaneous mutant that was able to propagate on a strain that *Staphylococcus* phage K was ineffective against; and 'Fred*710' was derived from 'Free' by its ability to propagate on a strain that 'Free' was ineffective against.

About 10 μg of DNA for each phage was received precipitated in alcohol.

Library generation for the 454 FLX sequencing was carried out according to the manufacturer's standard protocols (Roche/454 Life Sciences, Branford, Conn. 06405, USA). For example, the high molecular phage DNAs were sheared randomly by nebulization to fragments ranging in size from 400 bp to 900 bp. These fragments were end polished and the 454 A and B adaptors with the respective MIDs (multiplex identifiers) that are required for the emulsion PCR and sequencing were added to the ends of the fragments by ligation. The concentrations of the resulting fragment libraries were then measured by fluorometry, mixed in equal amounts and sequenced on 1/8 picotiterplate (PTP) on the GS FLX using the Roche/454 Titanium chemistry. A total of 105773 sequence reads with an average read length of 349.29 nucleotides, a total of 36.9 Mb sequence data, were obtained.

b) Assembly of the Sequences

The sequence reads of the individual phages were then sorted and assembled using the Roche/454 Newbler software at default settings (454 Life Sciences Corporation, Software release 2.3 (091027_1459)).

The results of the Newbler assembly are described in Table 1.

TABLE 1

Results of the Newbler assembly

|  | Fred | Fred* | Fred*710 |
|---|---|---|---|
| Total no. of reads | 11917 | 3817 | 88878 |
| Total no. bases | 3978979 | 1254392 | 30303252 |
| No. of reads assembled | 11716 | 3652 | 87016 |
| No. of contigs | 1 | 22 | 1 |
| No. of bases(contig length) | 139828 | 138287 | 139824 |

The difference of the read numbers in the assembly from the ones mentioned above results mainly from the short reads and those that could not be unambiguously identified and hence not included in the assembly. The uneven read distribution reflects the methodological inaccuracy in the determination of extremely low absolute concentrations.

c) Gap Closure and Finishing in Fred*

For gap closure, editing and comparison of the individual sequences, the assemblies of the three phages were transferred to the Staden Package suite of software (Staden Package 1-7-1b, Gap v.4.11, Staden R, Beal K F, Bonfield J K (2000) "The Staden package, 1998", Methods Mol. Biol. 132: 115-130).

A total of 192 Sanger reads were added to the Fred* Newbler assembly to close the gaps and to increase coverage on thinly sequenced stretches. This raised the average coverage from about 7 fold to about 10 fold (for comparison, after Newbler assembly, coverage in Fred was 25 fold and 189 fold in Fred*710).

d) Editing and Comparison of the Three Phages to *Staphylococcus* Phage K (Accession number: AY176327.1)

The assemblies were inspected manually and arranged in such a manner that they all begin at the same point in sequence as the published phage K sequence. The finished sequences were then aligned and compared individually to the phage K sequence and to each other. All three Fred phages carry a 9547 bp insertion that is not present in phage K. The insertion begins at position 116111 of the phage K sequence. Additionally eight point mutations were identified in Fred*710. These sequences suggest that Fred* is identical to Fred. However, the terminal repeat sequences of the phage genomes could not be resolved. The results of the comparison are summarized in FIG. 1 and Table 2.

TABLE 2

Comparison of Fred*710 with wild-type *Staphylococcus* bacteriophage K

| (Position) Base substitution | Amino acid substitution | Phage K protein affected |
|---|---|---|
| (18554) phage K-C: Fred*710-T | Phage K-V:Fred*710-M | Region between ORF 18 and ORF 19 |
| (40894) phage K-G: Fred*710-A | None predicted | Region between ORF 41 and ORF 42 |
| (78197) phage K-G: Fred*710-A | Phage K-G:Fred*710-R | ORF 68-hypothetical protein |
| (99388) phage K-G: Fred*710-C | None predicted | ORF 86/ORF 88/ORF 90-putative DNA polymerase |
| (102111) phage K-G: Fred*710-A | Phage K-G:Fred*710-R | ORF 92-hypothetical protein |
| (103720) phage K-T: Fred*710-C | Silent substitution | ORF 93-hypothetical protein; putative DNA |
| (105975) phage K-C: Fred*710-T | Phage K-A:Fred*710-V | ORF 96-putative major tail protein |
| (109329) phage K-A: Fred*710-G | Phage K-K:Fred*710-E | ORF 100-hypothetical protein | e) Verification of the Point Mutations and the Presence of Insertion by PCR

To verify the presence of the identified base substitutions and the existence of the insertion in the three Fred phages, primers were designed to generate PCR products across the positions in question (for primer sequences see Table 3). The PCR products were generated from each phage DNA and sequenced by conventional Sanger technique and the resulting sequences aligned and compared to the phage sequences. The eight substitutions in Fred*710 were all confirmed and no other substitutions were found in the PCR products. A PCR product across each of the boundaries of the insertion was obtained for all three Fred phages indicating the existence of the insertion in all three cases and was confirmed by Sanger sequencing of the six respective PCR products.

TABLE 3

Primers used for the verification of the point mutations and the existence of the insertion.

| Position | Sequence | SEQ ID No. | (Position) Melting temperature |
|---|---|---|---|
| 18554f | TGGCATAGCAAGAGCTTCATCAAC | 1 | (18305-18328) $T_m$ 64,83 |
| 18554r | AGCAGAAAGTGTCAAGGGAGTTAG | 2 | (19117-19140) $T_m$ 60,34 |
| 40894f | CTAGATGCGGAACCCGGTAG | 3 | (40559-40578) $T_m$ 61,88 |
| 40894r | TGCAGGGTCAATACCATATAAAGC | 4 | (41245-41269) $T_m$ 61,36 |
| 78197f | TTGGACTTCACCAAAAACATCC | 5 | (77956-77977) $T_m$ 61,11 |
| 78197r | ACGCAGGGCTGTACTGAAATC | 6 | (78553-78573) $T_m$ 61,57 |
| 99388f | GTTCCGTTGCTCACGGTAAAC | 7 | (98985-99005) $T_m$ 61,82 |
| 99388r | TCCCCATTTAAGAATGATTGTAGC | 8 | (99510-99533) $T_m$ |

TABLE 3-continued

Primers used for the verification of the point mutations and the existence of the insertion.

| Position | Sequence | SEQ ID No. | (Position) Melting temperature |
|---|---|---|---|
| 102111f | TCTCAGCAACTGAAGCATTCC | 9 | (101782-101802) $T_m$ 60,53 |
| 102111r | ACCTGTGAATCATCAACACTGC | 10 | (102346-102367) $T_m$ 60,04 |
| 103720f | ACCAAAGGAGCATGGAGAAAC | 11 | (103517-103537) $T_m$ 60,49 |
| 103720r | GGGAATCCACCTTCTTCAATG | 12 | (103960-103980) $T_m$ 60,68 |
| 105975f | TTCTCAAATGATTCAGGAGAGTCAG | 13 | (105737-105761) $T_m$ 61,10 |
| 105975r | CCATTACTTTCCCCTCCTTTTC | 14 | (106437-107458) $T_m$ 60,17 |
| 109329f | GGTAAGTCAAGGACAACCTCCAC | 15 | (108829-108851) $T_m$ 61,15 |
| 109329r | AGGTGTTCCTCCCGGTATTG | 16 | (109666-109685) $T_m$ 61,12 |
| 116111f | ACAGCATACGTTCTAAAGGAACAAG | 17 | (115794-115818) $T_m$ 60,12 |
| 116111r | CCCTACGATTATTTGGGCTAAAG | 18 | (116565-116587) $T_m$ 60,21 |
| 125658f | AGCTGATAAAGACCCTAGAACAACG | 19 | (125182-125206) $T_m$ 61,29 |
| 125658r | TGTAACCACCGCTAATACAATCTG | 20 | (126026-126049) $T_m$ 60,30 | f) Annotation

Figure 2:
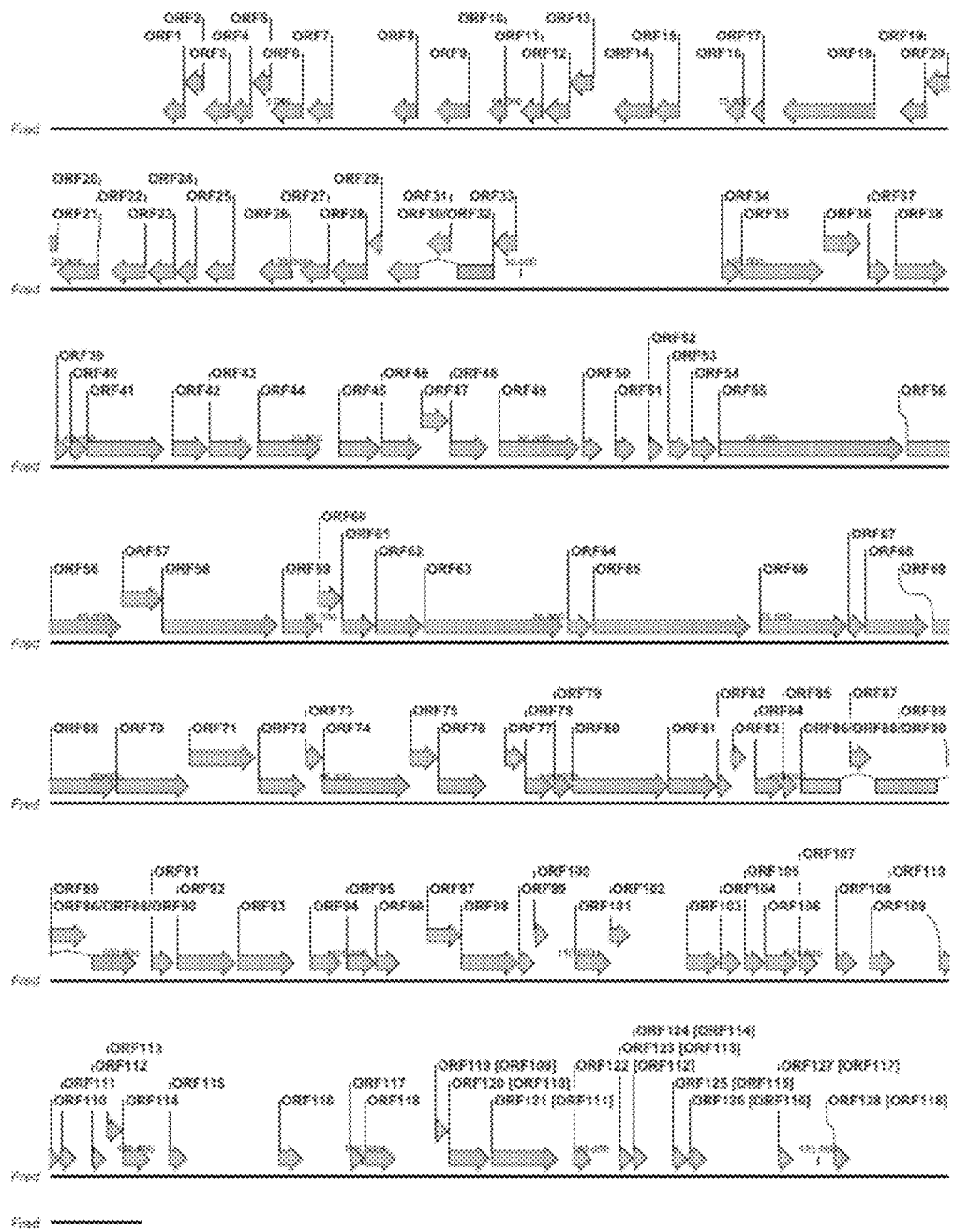
FIG. 2: Open Reading Frames identified in sequenced DNA of bacteriophage 'Fred'. Numbering in square brackets denotes equivalent *Staphylococcus* bacteriophage K ORFs.

The open reading frames in the Fred and Fred*710 sequences were identified using GeneMark software available at the world wide web address:exon.biology.gatech.edu. The individual reading frames were each then run against the NCBI genbank using BLAST and the highest scoring matches were then attributed to the respective ORF. As most of the sequences were identical to Staphylcoccus phage K, most of the annotation is homologous to phage K. The results of the annotation were then used to compile a genbank file that can be visualized using the CLC Bio Sequence viewer available at the world wide web address: clcbio.com. FIG. 2 shows the identified ORFs in Fred.

The invention claimed is:

1. A *Staphylococcus* bacteriophage K mutant, which comprises one or more mutations within one or more of the following regions, corresponding to the nucleotide sequence of wild-type *Staphylococcus* bacteriophage K, selected from:

a) the region between ORF 18 and ORF 19; and/or
   b) the region between ORF 41 and ORF 42; and/or
   c) ORF 68; and/or
   d) an overlapping region within ORF 86/88/90; and/or
   e) ORF 92; and/or
   f) ORF 93; and/or
   g) ORF 96; and/or
   h) ORF 100.

2. A bacteriophage according to claim 1, wherein said mutation occurs within ORF 96 of the corresponding nucleotide sequence of wild-type *Staphylococcus* bacteriophage K.

3. A bacteriophage according to claim 2, wherein said mutation is a C105975T point mutation of the corresponding nucleotide sequence of wild-type *Staphylococcus* bacteriophage K.

4. A bacteriophage according to claim 3, which additionally comprises one or more of the following point mutations:

C18554T, G40894A, G78197A, G99388C, G102111A, T103720C and/or A109329G of the corresponding nucleotide sequence of wild-type *Staphylococcus* bacteriophage K.

5. A bacteriophage according to claim 1, wherein said mutation comprises one or more of the following point mutations: C18554T, G40894A, G78197A, G99388C, G102111A, T103720C, C105975T and A109329G of the corresponding nucleotide sequence of wild-type *Staphylococcus* bacteriophage K.

6. A bacteriophage according to claim 1 which additionally comprises a further mutation within the nucleotide sequence, wherein said further mutation comprises an insertion at position 116111 of the corresponding nucleotide sequence of wild-type *Staphylococcus* bacteriophage K.

7. A bacteriophage according to claim 6, wherein said insertion is at least 9000 base pairs in length.

8. A bacteriophage according to claim 7, wherein said insertion is 9547 base pairs in length.

9. A bacteriophage according to claim 1, deposited under accession number: NCIMB 41894.

10. A pharmaceutical composition comprising the bacteriophage of claim 1 and a pharmaceutically acceptable carrier thereof.

11. A pharmaceutical composition according to claim 10, which comprises an additional bacteriophage.

12. A pharmaceutical composition according to claim 11, wherein the additional bacteriophage is P68.

13. A pharmaceutical composition according to claim 10, wherein said pharmaceutical composition is formulated for topical application to the nasal cavity of a mammal.

14. A pharmaceutical composition according to claim 10, wherein said bacteriophage is a pathogen of *Staphylococcus aureus*.

15. A pharmaceutical composition according to claim 14, wherein said bacteriophage is a pathogen of Methicillin-resistant *Staphylococcus aureus*.

16. A method of treating a bacterial infection, comprising applying a composition according to claim 10 to an infected surface.

17. A method according to claim 16, wherein said surface is the skin of a mammal.

18. A method according to claim 17, wherein said surface is the mucosal lining within the nasal cavity of a mammal.

* * * * *